US006787146B2

(12) United States Patent
Brake et al.

(10) Patent No.: US 6,787,146 B2
(45) Date of Patent: Sep. 7, 2004

(54) NEOSPORA VACCINE

(75) Inventors: David A. Brake, East Lyme, CT (US); Manuel Campos, Stonington, CT (US)

(73) Assignees: Pfizer Inc., New York, NY (US); Pfizer Products Inc., Groton, CT (US)

( * ) Notice: Subject to any disclaimer, the term of this patent is extended or adjusted under 35 U.S.C. 154(b) by 0 days.

(21) Appl. No.: 10/036,351

(22) Filed: Nov. 9, 2001

(65) Prior Publication Data

US 2002/0058046 A1 May 16, 2002

Related U.S. Application Data

(62) Division of application No. 09/138,985, filed on Aug. 24, 1998, now abandoned.
(60) Provisional application No. 60/056,956, filed on Aug. 26, 1997.

(51) Int. Cl.$^7$ ............................................. A61K 39/002
(52) U.S. Cl. .............................. 424/269.1; 424/265.1; 424/184.1; 424/193.1
(58) Field of Search .................... 424/269.1, 265.1, 424/184.1, 193.1

(56) References Cited

U.S. PATENT DOCUMENTS

| | | | |
|---|---|---|---|
| 5,707,617 A | | 1/1998 | Conrad et al. |
| 5,889,166 A | * | 3/1999 | Conrad et al. |

FOREIGN PATENT DOCUMENTS

| | | | |
|---|---|---|---|
| EP | 0734731 | | 10/1996 |
| EP | 0764446 | | 3/1997 |
| WO | 9525541 | | 9/1995 |
| WO | 95/25541 | * | 9/1995 |
| WO | 9717082 | | 5/1997 |

OTHER PUBLICATIONS

Barr et al. J. Vet. Diagnosis. 1993. 6(2): 7308.*
Lindsay et al. Am. J. Vet. Res., 1995. 56(9): 1176–1180.*
Lindsay et al. J. Parasitol. 1990. 76(3): 410–413.*
Barta et al. Parasitol. Res. 1992. 78: 689–694.*
Barr et al., 1994, J. Vet. Diagn. Invest. 6:207–215, "Experimental reproduction of bovine fetal Neospora infection and death with a bovine *Neospora* isolate."
Cole et al., 1995, J. Parasitol. 81:730–732, "Vertical transmission of *Neospora caninum* in mice."
Conrad et al., 1993, Parasitol. 106:239–249, "In vitro isolation and characterization of a Neospora sp. from aborted bovine foetuses."
Dubey and Lindsay, 1993, Parasitol. Today 9:452–458, "Neosporosis."
Lindsay et al., 1995, J. Parasitol. 81:313–315, "Mouse model for central nervous system *Neospora caninum* infections."
Lindsay et al., 1995, Am. J. Vet. Res. 56:1176–1180, "Abortions, fetal deaths and stillbirths in pregnant pygmy goats inoclated with tachyzoites of *Neospora caninum*."
Lindsay and Dubey, 1989, J. Parasitol. 75:772–779, "*Neospora caninum* (Protozoa: Apicomplexa) infections in mice."
Lindsay and Dubey, 1989, J. Parasitol. 75:163–165, "In vitro development of *Neospora caninum* (Protozoa: Apicomplexa) from dogs."
Lindsay and Dubey, 1990, J. Parasitol. 76:410–413, "Infections in mice with tachyzoites and bradyzoites of *Neospora caninum* (protozoa: Apicomplexa)."
Barta et al., 1992, Parasitol. Res. 78:689–694, "Characterization of anti–*Neopsora caninum* hyperijmmune rabbit serum by Western blot analysis and immunoelectron microscopy."
Baszler et al., 1996, J. Clin. Microbiol. 34(6):1423–1428, "Serological Diagnosis of Bovine Neosporosis by *Neospora caninum* Monoclonal Antibody–Based Competitive Inhibition Enzyme–Linkd Immunosorbent Assay."

* cited by examiner

Primary Examiner—Jennifer E. Graser
(74) Attorney, Agent, or Firm—Scully, Scott, Murphy & Presser

(57) ABSTRACT

The present invention provides an homogenate prepared from cells of Neospora, and vaccines against neosporosis prepared therefrom which are useful in the prevention of clinical disease and abortion in mammals.

9 Claims, 7 Drawing Sheets

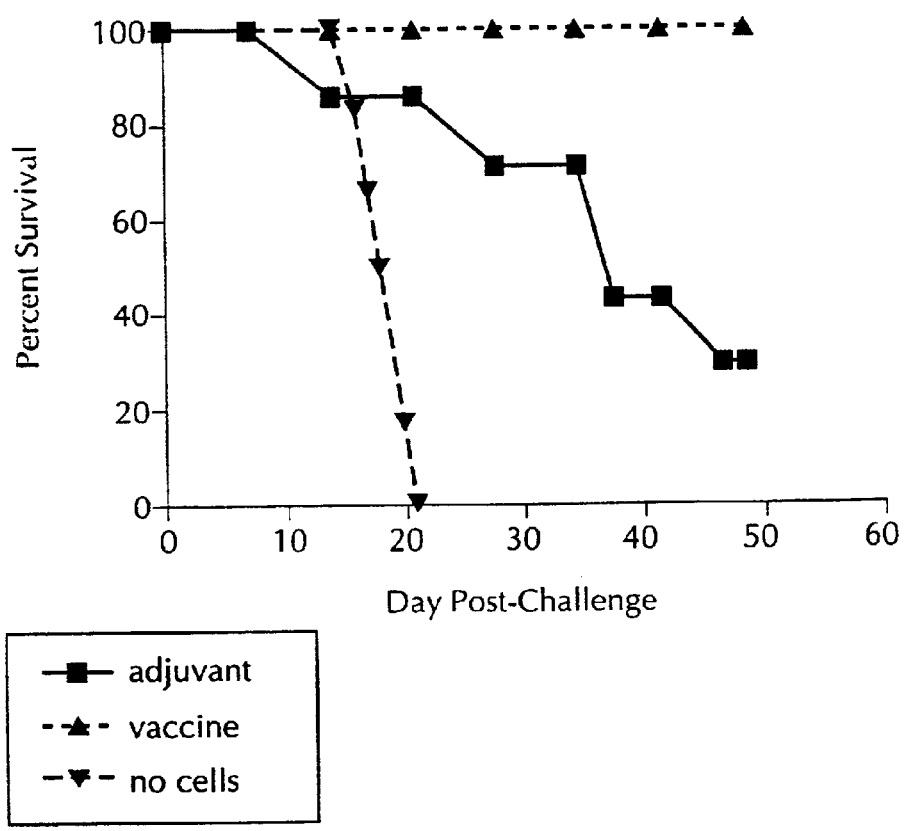

NEOSPORA VACCINE

This application is a divisional of U.S. patent application Ser. No. 09/138,985, filed Aug. 24, 1998, now abandoned, which claims the benefit of priority of U.S. Provisional Patent Application Ser. No. 60/056,956, filed on Aug. 26, 1997.

FIELD OF THE INVENTION

The present invention relates to a vaccine against the pathogenic protozoan Neospora which vaccine is useful in the prevention of clinical disease and abortion in mammals. The vaccine of the invention comprises an homogenate prepared from cells of a species of Neospora.

BACKGROUND OF THE INVENTION

Neosporosis in mammals is caused by infection with a pathogenic strain of the protozoan parasite Neospora, and has been recognized as a major cause of abortion, neonatal death, congenital infection, and encephalitic disease. Dubey and Lindsay, 1996, Vet. Parasitol. 67:1–59; Dubey and Lindsay, 1993, Parasitol. Today 9:452–458. *Neospora caninum* infects dogs and congenitally infects pups, often leading to paralysis. Tachyzoites of *N. caninum* have been isolated from naturally infected pups. Lindsay and Dubey, 1989, J. Parasitol. 75:163–165. Infection with Neospora is also a major cause of abortion in dairy cattle. Cases of neosporosis have also been reported in goats, sheep and horses.

Although *N. caninum* is superficially similar to the pathogen *Toxoplasma gondii*, *N. caninum* and *T. gondii* are distinguishable from each other both antigenically and ultrastructurally. Dubey and Lindsay, 1993, above. In addition, Neospora-like protozoan parasites isolated from the brains of aborted bovine fetuses and continuously cultured in vitro were shown to be antigenically and ultrastructurally distinct from both *T. gondii* and *Hammondia hammondi*, and most similar to *N. caninum*. Conrad et al., 1993, Parasitology 106:239–249. Furthermore, analysis of nuclear small subunit ribosomal RNA genes revealed no nucleotide differences between Neospora strains isolated from cattle and dogs, but showed consistent differences when compared to *T. gondii*, thus confirming the distinction between pathogens. Marsh et al., 1995, J. Parasitol. 81:530–535.

The etiologic role of a bovine isolate of Neospora in bovine abortion and congenital disease has been confirmed. Barr et al. 1994, J. Vet. Diag. Invest. 6:207–215. A rodent model of central nervous system neosporosis has been developed using inbred BALB/c mice infected with *N. caninum*. Lindsay et al, 1995, J. Parasitol. 81:313–315. In addition, models to study transplacental transmission of *N. caninum* in pregnant outbred and inbred mice have been described by Cole et al., 1995, J. Parasitol. 81:730–732, and by Long et al., 1996, J. Parasitol. 82:608–611, respectively. Furthermore, an experimental *N. caninum* pygmy goat model closely resembling naturally acquired Neospora-induced cattle abortion has been developed. Lindsay etal., 1995, Am. J. Vet. Res. 56:1176–1180.

WO 9525541 discloses a biologically pure culture of bovine Neospora, methods of detecting anti-Neospora antibodies and Neospora-specific nucleic acids, and a composition containing a bovine Neospora antigen and carrier for use as a vaccine.

An effective vaccine against neosporosis comprising an homogenate prepared from cells of Neospora has not previously been disclosed.

SUMMARY OF THE INVENTION

In a first aspect, the present invention provides an homogenate prepared from cells of Neospora, which homogenate is capable of inducing a protective response against neosporosis in a mammal.

In a second aspect, the present invention provides a vaccine to protect a mammal against neosporosis, comprising an immunologically effective amount of an homogenate prepared from cells of Neospora, which homogenate is capable of inducing a protective response against neosporosis in a mammal, and a veterinarily acceptable carrier. The vaccine of the present invention may further comprise one or more additional immunomodulatory components including, e.g., an adjuvant or cytokine.

In a third aspect, the present invention provides a method for preparing a vaccine that protects a mammal against neosporosis, comprising homogenizing cells of Neospora to form an homogenate capable of inducing a protective response against neosporosis in a mammal. and combining an immunologically effective amount of the homogenate with a veterinarily acceptable carrier in a form suitable for administration to the mammal.

In a fourth aspect, the present invention provides a method for protecting a mammal against neosporosis, comprising administering to the mammal a vaccine comprising an immunologically effective amount of an homogenate prepared from cells of Neospora, which homogenate is capable of inducing a protective response against neosporosis in a mammal, and a veterinarily acceptable carrier. The vaccine of the present invention may be administered to any mammalian species susceptible to infection and disease caused by Neospora, including but not limited to dogs, cows, goats, sheep and horses.

In a fifth aspect, the present invention provides a combination vaccine for protecting a mammal against neosporosis and, optionally, one or more other diseases or pathological conditions that can afflict the mammal, which combination vaccine comprises an immunologically effective amount of a first composition comprising an homogenate prepared from cells of Neospora, which homogenate is capable of inducing a protective response against neosporosis in a mammal; an immunologically effective amount of a second composition capable of inducing a protective response against a disease or pathological condition that can afflict the mammal; and a veterinarily acceptable carrier.

The second composition of the combination vaccine is selected based on its ability to induce a protective response against either neosporosis or another disease or pathological condition that can afflict members of the mammalian species, as known in the art. The combination vaccine of the present invention may further comprise one or more additional immunomodulatory components including, e.g., an adjuvant or cytokine, among others.

In a sixth aspect, the present invention provides a kit for vaccinating a mammal against neosporosis, comprising a first container having an immunologically effective amount of an homogenate prepared from cells of Neospora, which homogenate is capable of inducing a protective response against neosporosis in a mammal, and a second container having a veterinarily acceptable carrier or diluent suitable for mixing with the contents of the first container.

In a seventh aspect, the present invention provides antibodies specific to one or more antigenic components present in an homogenate prepared from cells of Neospora.

BRIEF DESCRIPTION OF THE DRAWINGS

FIG. 7. Post-challenge survival curves of athymic nude mice. Nude mice receiving DPBS alone (no splenocytes= "no cells"); nude mice receiving splenocytes from BALB/c mice that were injected with adjuvant alone ("adjuvant"); nude mice receiving splenocytes from BALB/c mice that were injected with the NSA preparation plus adjuvant ("vaccine") (n=6–7 mice/group). Results demonstrate that the transfer of cells from vaccinated BALB/c mice to nude mice results in adoptive protective immunity as shown by prolonged survival and significant protection against an NC-1 virulent challenge.

DETAILED DESCRIPTION OF THE INVENTION

Figure 1:
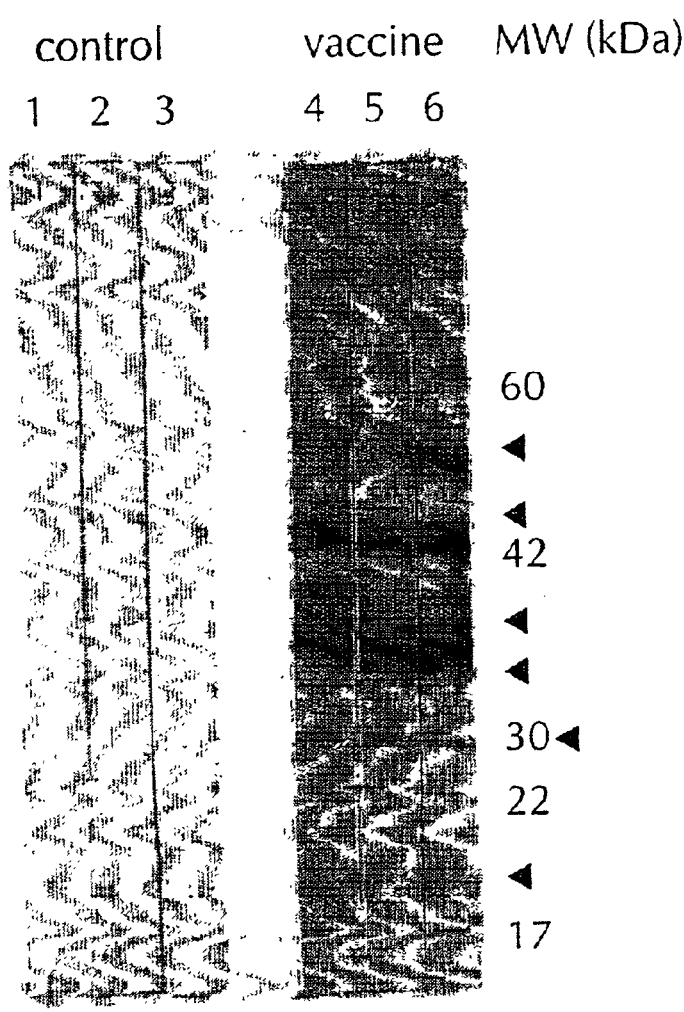
FIG. 1. Pre-challenge Western blot analysis of serum from BALB/c mice. A whole cell homogenate of NC-1 tachyzoites (the "NSA preparation") was fractionated by SDS-PAGE and transferred to PVDF membrane, which was then incubated with primary antiserum samples, followed by alkaline-phosphatase conjugated goat anti-mouse igG, and developed using the chromogenic substrate BCIP/NBT. Lanes 1–3= serum from mice administered adjuvant alone (control); lanes 4–6=serum from mice administered the NSA preparation plus adjuvant (vaccine); molecular weight standards indicated. Serum from immunized mice contains antibodies that are reactive with NSA preparation proteins having molecular weights of about 17–19, 28–30, 33, 37, 46, 48 and 56 kD.
Figure 2A:
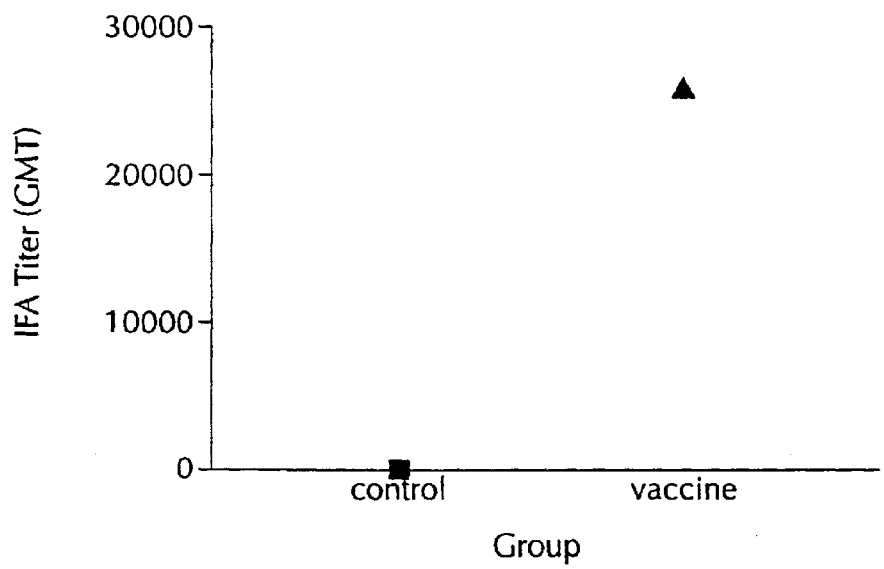
FIGS. 2A–2B Pre-challenge (A) and postchallenge (B) immunofluorescence antibody (IFA) titers. Serum from animals on day 21 post-immunization (day 0 pre-challenge) and day 21 post-challenge were added to wells containing NC-1 tachyzoites. Wells were then incubated with $(Fab)_2$ fluorescein isothiocyanate-conjugated anti-mouse IgG+IgM (Kirkegaard & Perry, Gaithersburg, Md.), washed, and examined by epifluorescent microscopy. Antibody titer is based on the highest dilution of immune serum producing a detectable fluorescence. Results show higher mean IFA antibody titers in vaccinated animals pre-challenge (2A) and significantly higher IFA antibody titers post-challenge (2B) ($P<0.001$) when compared to controls. In 2B, with $10^6$ challenge, control geometric mean titer (GMT)=2,691; vaccine GMT=25,600. With $10^7$ challenge, control GMT=5,382; vaccine GMT=72,408.
Figure 2B:
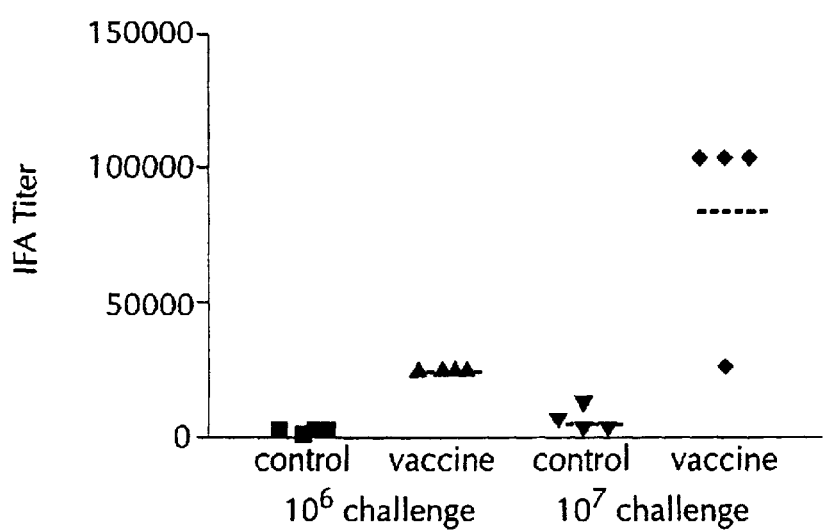

Applicants have discovered that an homogenate prepared from cells of Neospore is capable of inducing a protective response against neosporosis in mammals. The present invention thus provides an homogenate prepared from cells of Neospora, which homogenate is capable of inducing a protective response against neosporosis in a mammal.

The present invention further provides a vaccine to protect a mammal against neosporosis, comprising an immunologically effective amount of an homogenate prepared from cells of Neospora, which homogenate is capable of inducing a protective response against neosporosis in a mammal, and a veterinarily acceptable carrier.

As used herein, the term "neosporosis" refers to infection of a mammal by cells of a species or strain of Neospora, or to any clinical symptom, condition, event or pathology associated with or resulting from infection of the mammal by cells of a species or strain of Neospora.

The phrase "capable of inducing a protective response" is used broadly herein to include the induction or enhancement of any immune-based response in the animal in response to vaccination, including either an antibody or cell-mediated immune response, or both, that serves to protect the vaccinated animal against neosporosis. The terms "protective response," "protection against," "protect," etc., as used herein, refer not only to the absolute prevention of neosporosis or absolute prevention of infection by a neosporosis-causing pathogen, but also to any detectable reduction in the degree or rate of infection by such a pathogen, any detectable reduction in the incidence of death or any detectable increase in survival time following infection with a virulent strain of the pathogen, any detectable reduction in the severity of the disease or in any symptom or condition resulting from infection with the pathogen, including, e.g., any detectable reduction in the rate of formation or in the absolute number of lesions in one or more tissues in the vaccinated animal, or any detectable reduction in the occurrence of abortion or the transmission of infection from a parent mammal to its offspring.

The phrase "immunologically effective amount" refers to that amount or dose of vaccine, homogenate, antigen or NSA preparation capable of inducing a protective response against neosporosis when administered to a member of a mammalian species after either a single administration, or after multiple administrations.

Preparation Of Neospora Antigen

The invention is based on the discovery that an homogenate prepared from cells of Neospora is capable of inducing a protective response against neosporosis in mammals. The cells used to produce the homogenate in the vaccine of the present invention may be derived from any strain of any species of the genus Neospora, which cells may or may not be pathogenic, where the homogenate is capable of inducing a protective response against neosporosis in mammals. In a preferred embodiment, the species of Neospora is *N. caninum*. A non-limiting example of a strain of *N. caninum* from which an homogenate may usefully be prepared is strain NC-1, which is available in infected MARC145 monkey kidney cells, deposited on Nov. 6, 1996 with the American Type Culture Collection, located at 10801 University Boulevard, Manassas, Va. 2-110-2209, USA (ATCC Accession No. CRL-12231), and which encompasses strains derived from NC-1 by one or more in vitro and/or in vivo passages. Strain NC-1 is also described in Dubey et al., 1988, J. Am. Vet. Med. Assoc. 193: 1259–1263, which publication is incorporated herein by reference. Strains of Neospora for use according to the present invention may alternatively be isolated from organs, tissues or body fluids of infected animals using standard isolation techniques, such as those described in the publications reviewed above.

In a non-limiting embodiment, the vaccine of the present invention may be prepared using homogenates of cells of other species of Neospora that are immunologically equivalent to *N. caninum* or using homogenates of cells of other strains of *N. caninum* that are immunologically equivalent to *N. caninum* strain NC-1. A species of Neospora is "immunologically equivalent" to *N. caninum* where an homogenate prepared from the cells of the immunologically equivalent species is capable of inducing in a mammal the production of antibodies that recognize one or more antigenic components present in an homogenate of cells of *N. caninum*, as determined, e.g., by Western blot analysis, and where the homogenate of cells of the immunologically equivalent species is capable of inducing a protective response against neosporosis in mammals. Likewise, a strain of *N. caninum* is "immunologically equivalent" to *N. caninum* strain NC-1 where an homogenate prepared from the cells of the immunologically equivalent strain is capable of inducing in a mammal the production of antibodies that recognize one or more antigenic components present in an homogenate of cells of *N. caninum* strain NC-1 (see FIG. 1), and where the homogenate prepared from cells of the immunologically equivalent strain is capable of inducing a protective response against neosporosis in mammals.

Cells of Neospora for use according to the present invention may be utilized directly and without further modification. Alternatively, such cells may be modified, e.g., by genetic manipulation, to add, increase, delete or reduce the expression of one or more metabolic pathways or products, or antigenic properties, such as, e.g., a particular surface antigen or virulence factor, or otherwise modify said pathways, products or properties. Such pathways, products or properties, the expression of which may usefully be added, increased or otherwise modified in the cells, are preferably those which serve to trigger or enhance the induction of a protective response against neosporosis in a mammal vaccinated with the corresponding homogenate. For example, cells of Neospora may be genetically modified to add or detectably increase the expression of one or more antigenic components which are useful to trigger or enhance the induction of a protective response. In a non-limiting embodiment, cells of Neospora are genetically modified to add or detectably increase the expression of one or more immunodominant antigens, such as those visualized by SDS-PAGE separation and Western blot analysis of the NSA preparation as described below, including those antigens identified as having molecular weights selected from the group consisting of about 17–19, 28–30, 33, 37, 46, 48 and 56 kD.

Alternatively or additionally, cells may be modified to delete or detectably reduce the expression of one or more antigenic components normally associated with unmodified cells of Neospora or an homogenate prepared therefrom. In a non-limiting embodiment, cells of Neospora are genetically modified to delete or detectably reduce the expression of one or more antigenic components, such as those that may be visualized by SDS-PAGE separation and Western blot analysis of the NSA preparation as described below, and including those antigenic components identified as having molecular weights selected from the group consisting of about 17–19, 28–30, 33, 37, 46, 48 and 56 kD. In this manner, vaccines may be produced that are "marked" or "tagged," thereby allowing for animals that have been vaccinated to be distinguished from those that have naturally been infected with the pathogen.

Methods by which protozoan cells, such as those of Neospora, may be genetically modified are generally known in the art, and include the introduction of random mutations, e.g., by exposure to chemical mutagens or radiation, followed by selection for a desired mutant phenotype. Alternatively, or additionally, Neospora cells may be modified by targeted genetic modification as carried out by known procedures such as, e.g., by homologous recombination as described, e.g., by Cruz and Beverley, 1990, Nature 348:171–173; Cruz et al., 1991, Proc. Natl. Acad. Sci. USA 88:7170–7174; Donald and Roos, 1994, Mol. Biochem. Parasitol. 63:243–253; and Titus et al., 1995, Proc. Natl. Acad. Sci. USA 92:10267–10271, which publications are incorporated herein by reference. Such genetic modification is within the skill in the art and may be carried out using generally known recombinant techniques such as those described, e.g., in Maniatis, et al., 1989, *Molecular Cloning, A Laboratory Manual*, Cold Spring Harbor Laboratory Press, Cold Spring Harbor, N.Y.; Ausubel, et al., 1989, *Current Protocols In Molecular Biology*, Greene Publishing Associates & Wiley Interscience, N.Y.; and Sambrook, et al., 1989, *Molecular Cloning: A Laboratory Manual*, 2d ed., Cold Spring Harbor Laboratory Press, Cold Spring Harbor, N.Y., which publications are incorporated herein by reference.

Once obtained, cells of Neospora for use in the present invention may be cultured in vitro by infecting any receptive cell line, preferably a mammalian cell line, with tachyzoites of the species or strain of Neospora according to known techniques described in the art. Mammalian cell lines in which tachyzoites of Neospora can be cultured include, e.g., human foreskin fibroblasts (Lindsay et al., 1993, Am. J. Vet. Res. 54:103–106), bovine cardiopulmonary aortic endothelial cells (Marsh et al., 1995, above), bovine monocytes (Lindsay and Dubey, 1989, above), monkey kidney cells, among others. For example, tachyzoites of *N. caninum* may be cultured in monolayers of Hs68 human foreskin fibroblast cells (ATCC Accession No. CRL-1635) (Lindsay et al., 1993, above). Bradyzoites may be similarly cultured and manipulated.

Mammalian cell cultures can be grown, and cell cultures that have been infected with Neospora can be maintained, in any of several types of culture media described in the art. For example, stationary monolayer cultures of bovine cardiopulmonary aortic endothelial cells infected with tachyzoites of *N. caninum* may be grown in Dulbecco's Minimum Essential Medium (DMEM: Gibco Laboratories, N.Y.), supplemented with 10% (v/v) heat-inactivated fetal bovine serum (FBS) or adult equine serum (ES), 2 mM L-glutamine, 50 U/ml penicillin, and 50 µg/ml streptomycin (Conrad et al., 1993, above). Monolayers of Hs68 human foreskin fibroblast cells may be maintained in RPMI 1640 containing 2% (v/v) FBS, 1.0 mM sodium pyruvate, $1 \times 10^4$ U/ml penicillin, $1 \times 10^4$ µg/ml streptomycin, $5 \times 10^{-2}$ mM 2-mercaptoethanol and 0.3 mg/ml L-glutamine (maintenance medium). Monolayer cultures of Hs68 human foreskin fibroblast cells infected with Neospora may be maintained in identical media, but in which the FBS is increased to 10% (v/v) (growth medium).

Neospora-infected monolayer cultures of mammalian cells are typically maintained under standard tissue culture conditions such as, e.g., at 37° C. and 5% $CO_2$. Tachyzoites are typically passaged to uninfected monolayer cultures when 70–90% of the mammalian cells in the culture have become infected, which may be determined microscopically using standard techniques. Tachyzoites may be collected from the infected mammalian cell cultures by lysing the host cells using any standard technique and collecting the tachyzoites, e.g., by filtration or by centrifugation.

Cells which may be used to produce the cell homogenate of the invention are preferably tachyzoites, but may alternatively be bradyzoites or oocysts, or some combination thereof. In addition, cells for use in the present invention may either be viable cells or cells which have previously been inactivated, e.g., by treatment with a chemical inactivating agents such as formaldehyde or glutaraldehyde, among others, or by treatment with radiation, or by exposure to extreme pH or temperature, or some combination thereof.

The production of the homogenate of the invention is not limited to any particular method of homogenization or disruption. Rather, cells of Neospora may be homogenized or disrupted using any technique known in the art including but not limited to freeze/thawing, osmotic bursting, grinding, sonication, use of a polytron, blender or tissue homogenizer, or some combination thereof.

As used herein, the term "homogenate" refers to a preparation prepared by homogenizing or disrupting whole cells of Neospora. The homogenate of the present invention may comprise all of the components produced by the homogenization or disruption of whole Neospora cells, thus representing a "whole cell" preparation. Alternatively, the homogenate of the present invention may consist of a fraction of the total contents of homogenized or disrupted Neospora cells, which fraction is prepared from the whole cell preparation using one or more fractionation, isolation or purification steps known in the art, including, e.g., centrifugation, filtration, dialysis, preparative gel electrophoresis, affinity chromatography, ion exchange chromatography, size exclusion chromatography, ammonium sulfate precipitation, or some combination thereof, where the resulting fraction of the whole cell preparation retains the ability to induce a protective response against neosporosis in mammals. Such a fraction may be an enriched membrane fraction or, alternatively, a fraction enriched in soluble cytoplasmic components. Such fractions are easily prepared and tested using nothing more than routine preparative and screening procedures.

Preparation and Use of Vaccines

The present invention provides a vaccine against neosporosis, comprising an immunologically effective amount of an homogenate prepared from cells of Neospora, which homogenate is capable of inducing a protective response against neosporosis in a mammal, and a veterinarily acceptable carrier.

The present invention further provides a method for preparing a vaccine that protects a mammal against neosporosis, comprising homogenizing cells from Neospora to produce a homogenate capable of inducing a protective response against neosporosis in a mammal, and combining an immunologically effective amount of the homogenate with a veterinarily acceptable carrier in a form suitable for administration to the mammal.

The vaccine may simply comprise a cell homogenate prepared in culture fluid taken directly from a Neospora cell culture, which is then administered directly to the mammal, or may instead comprise a cell homogenate combined with a veterinarily acceptable carrier selected from those known in the art appropriate to the route of administration. For example, the vaccine of the present invention may be formulated following accepted convention by combining the homogenate or a fraction thereof with standard buffers, carriers, stabilizers, diluents, preservatives, and/or solubilizers. The vaccine may also be formulated to facilitate sustained release. Diluents may include water, saline, dextrose, ethanol, glycerol, and the like. Additives for isotonicity may include sodium chloride, dextrose, mannitol, sorbitol, and lactose, among others. Stabilizers may include albumin, among others. Suitable other vaccine vehicles and additives are known, or will be apparent, to those skilled in the art. See, e.g., Remington's *Pharmaceutical Science,* 18th ed., 1990, Mack Publishing, which is incorporated herein by reference.

The vaccine of the present invention may further comprise one or more additional immunomodulatory components such as, e.g., an adjuvant or cytokine. Non-limiting examples of adjuvants include the RIBI adjuvant system (Ribi Inc., Hamilton, Mont.), alum, mineral gels such as aluminum hydroxide gel, oil-in-water emulsions, water-in-oil emulsions such as, e.g., Freund's complete and incomplete adjuvants, Block co polymer (CytRx, Atlanta Ga.), QS-21 (Cambridge Biotech Inc., Cambridge Mass.) and SAF-M (Chiron, Emeryville Calif.), AMPHIGEN® adjuvant, saponin, Quil A or other saponin fraction, monophosphoryl lipid A, and Avridine lipid-amine adjuvant. Specific non-limiting examples of oil-in-water emulsions useful in the vaccine of the invention include SEAM62 and SEAM ½, the components of which are set forth below. Other immunomodulatory agents which may be included in the vaccine include, e.g., one or more interleukins, interferons, or other known cytokines. The vaccine may be stored in solution or, alternatively, in lyophilized form to be reconstituted with a sterile diluent solution prior to administration.

The vaccine of the present invention may optionally be formulated for the sustained release of the antigen. Examples of such sustained release formulations include homogenate in combination with composites of biocompatible polymers, such as, e.g., poly(lactic acid), poly(lactic-co-glycolic acid), methylcellulose, hyaluronic acid, collagen and the like. The structure, selection and use of degradable polymers in drug delivery vehicles have been reviewed in several publications, including A. Domb et al., 1992, Polymers for Advanced Technologies 3: 279–292, which is incorporated herein by reference. Additional guidance in selecting and using polymers in pharmaceutical formulations can be found in the text by M. Chasin and R. Langer (eds), 1990, "Biodegradable Polymers as Drug Delivery Systems" in: *Drugs and the Pharmaceutical Sciences*, Vol. 45, M. Dekker, N.Y., which is also incorporated herein by reference. Alternatively, or additionally, the homogenate may be microencapsulated to improve administration and efficacy. Methods for microencapsulating antigens are well-known in the art, and include techniques described, e.g., in U.S. Pat. Nos. 3,137,631; 3,959,457; 4,205,060; 4,606,940; 4,744,933; 5,132,117; and International Pub. WO 95/28227, all of which are incorporated herein by reference.

Liposomes may also be used to provide for the sustained release of the homogenate of the invention. Details concerning how to make and use liposomal formulations can be found in, among other places, U.S. Pat. Nos. 4,016,100; 4,452,747; 4,921,706; 4,927,637; 4,944,948; 5,008,050; and 5,009,956, all of which are incorporated herein by reference.

The present invention further provides a method for protecting a mammal against neosporosis, comprising administering to the mammal a vaccine comprising an immunologically effective amount of an homogenate prepared from cells of Neospora, which homogenate is capable of inducing a protective response against neosporosis in a mammal, and a veterinarily acceptable carrier.

The vaccine is preferably administered parenterally, e.g., either by subcutaneous or intramuscular injection. However, the vaccine may instead be administered by intraperitoneal or intravenous injection, or by other routes, including, e.g., orally, intranasally, rectally, vaginally, intra-ocularly, or by a combination of routes. The skilled artisan will know how to formulate the vaccine composition according to the route chosen.

An effective dosage may be determined by conventional means, starting with a low dose of homogenate and then increasing the dosage while monitoring the effects. Numerous factors may be taken into consideration when determining an optimal dose per animal. Primary among these is the species, the size of the animal, the age of the animal, the general condition of the animal, the presence of other drugs in the animal, the virulence of a particular species or strain of Neospora against which the animal is being vaccinated, and the like. The actual dose is preferably chosen after consideration of the results from other animal studies.

Vaccine regimens may also be selected based on the above-described factors. The vaccine of the invention may be administered at any time during the life of a particular animal depending upon several factors including, e.g., the timing of an outbreak of neosporosis among other animals, etc. The vaccine may be administered to animals of weaning age or younger, or to more mature animals, e.g., as a pre-breeding vaccine to protect against Neospora-related congenital disease or abortion.

Effective protection may require only a primary vaccination, or one or more booster vaccinations may be needed for full protection. One method of detecting whether adequate immune protection has been achieved is to determine seroconversion and antibody titers in the animal after vaccination. The timing of vaccination and the number of boosters, if any, will preferably be determined by a veterinarian based on analysis of all relevant factors, some of which are described above.

The amount of homogenate in the vaccine preferably ranges from about 10 to about 1,000 $\mu$g protein/ml, and more preferably from about 100 to about 500 $\mu$g protein/ml. A suitable dosage size ranges from about 0.5 ml to about 10.0 ml, and more preferably from about 1.0 ml to about 5.0 ml. Generally, on a per dose basis, the amount of cell homogenate administered to an animal is preferably from about 10 to about 1,000 $\mu$g protein, and more preferably from about 100 to about 500 $\mu$g protein.

The vaccine of the present invention is useful to protect mammals against infection or disease caused by Neospora. As used herein, the term "mammal" refers to any mammalian species that can be protected against neosporosis using the vaccine of the invention, including dogs, cows, goats, sheep and horses, among others. The vaccine is useful to protect both pregnant and non-pregnant mammals.

The present invention further provides a combination vaccine for protecting a mammal against neosporosis and, optionally, one or more other diseases or pathological conditions that can afflict the mammal, which combination vaccine comprises an immunologically effective amount of a first composition comprising an homogenate prepared from cells of Neospora, which homogenate is capable of inducing a protective response against neosporosis in a mammal; an immunologically effective amount of a second composition capable of inducing a protective response against a disease or pathological condition that can afflict the mammal; and a veterinarily acceptable carrier, such as described above.

The second composition of the combination vaccine is selected based on its ability to induce a protective response against either neosporosis or another disease or pathological condition which afflicts members of the mammalian species, as known in the art. Any immunogenic composition known to be useful in a vaccine composition in the particular mammalian species may be used in the second composition of the combination vaccine. Such immunogenic compositions include but are not limited to those that provide protection against pathogens selected from the group consisting of bovine herpes virus (infectious bovine rhinotracheitis), bovine respiratory syncitial virus, bovine viral diarrhea virus, parainfluenza virus types I, II, or III, Leptospira spp., Campylobacter spp., *Staphylococcus aureus, Streptococcus agalactiae*, Mycoplasma spp., Klebsielia spp., Salmonella spp., rotavirus, coronavirus, rabies, *Pasteurella haemolytica, Pasteurella multocida*, Clostridia spp., Tetanus toxoid, *E. coli*, Cryptosporidium spp., Eimeria spp., and other eukaryotic parasites, among others.

The combination vaccine of the present invention may further comprise one or more additional immunomodulatory components including, e.g., an adjuvant or cytokine, and may optionally be formulated for sustained release or be stored in lyophilized form or both, as described above.

The present invention further provides a kit for vaccinating a mammal against neosporosis, comprising a first container having a vaccine comprising an immunologically effective amount of an homogenate prepared from cells of Neospora, which homogenate is capable of inducing a protective response against neosporosis in a mammal, and a second container having a veterinarily acceptable carrier or diluent suitable for mixing with the contents of the first container. The vaccine may be stored in lyophilized form to be reconstituted by addition of the carrier or diluent.

Anti-neospora Antibodies

The production of polyclonal and monoclonal antibodies that bind to one or more Neospora-specific antigenic components falls within the scope of the invention. Such antibodies may be specific to any of the antigenic components associated with Neospora cells or an homogenate prepared therefrom. In a non-limiting embodiment, antibodies may be raised against one or more of the antigenic components visualized in the Western blot of FIG. 1, including those antigenic components identified as having molecular weights selected from the group consisting of about 17–19, 28–30, 33, 37, 46, 48 and 56 kD. Such antibodies may be useful as reagents for the differential diagnosis of neosporosis, such as for detecting Neospora-specific antigens in histological sections, or in cell, tissue or fluid samples from an animal, such as, e.g., in ELISA or Western blot assays, or to quantify the amount of antigen in a vaccine preparation.

Antibodies may be raised against any of the antigenic components present in a homogenate of Neospora cells, such as those in the NSA preparation described below. Various host animals, including but not limited to cows, horses, rabbits, goats, sheep, and mice, may be used according to known immunological techniques to produce antibodies against one or more Neospora-specific antigenic components. Various adjuvants, such as those described above, may be used to increase the immunological response to enhance antibody production.

Polyclonal antibodies may be obtained from immunized animals and tested for specificity against Neospora-specific antigenic components using standard techniques. Alternatively, monoclonal antibodies to a Neospora-specific antigenic component may be prepared using any technique which provides for the production of antibody molecules by continuous cell lines in culture. These include but are not limited to the hybridoma technique originally described by Kohier and Milstein (Nature, 1975, 256: 495–497); the human B-cell hybridoma technique (Kosbor et al., 1983, Immunology Today 4:72; Cote et al., 1983, Proc. Natl. Acad. Sci. USA 80: 2026–2030); and the EBV-hybridoma technique (Cole et al., 1985, *Monoclonal Antibodies and Cancer Therapy*, Alan R. Liss, Inc., pp. 77–96). Alternatively, techniques described for the production of single chain antibodies (see, e.g., U.S. Pat. No. 4,946,778) can be adapted to produce Neospora antigen-specific single chain antibodies. These publications are incorporated herein by reference.

Antibody fragments that contain specific binding sites to a Neospora-specific antigenic component are also encompassed within the present invention, and may be generated by known techniques. Such fragments include but are not limited to F(ab')$_2$ fragments, which can be generated by pepsin digestion of an intact antibody molecule, and Fab fragments, which can be generated by reducing the disulfide bridges of the F(ab')$_2$ fragments. Alternatively, Fab expression libraries may be constructed (Huse et al., 1989, Science 246: 1275–1281) to allow rapid identification of Fab fragments having the desired specificity to a Neospora-specific antigen.

The antibodies and antibody fragments of the present invention may further comprise a detectable label such as a fluorescent tag, radioactive label or enzyme. as known in the art, to aid in the detection of specifically bound antibody in any of the aforementioned diagnostic assays.

Techniques for the production and use of monoclonal antibodies and antibody fragments are well-known in the art, and are additionally described, among other places, in Harlow and Lane, 1988, *Antibodies: A Laboratory Manual*, Cold Spring Harbor Laboratory, and in J. W. Goding, 1986, *Monoclonal Antibodies: Principles and Practice*, Academic Press, London, which are incorporated herein by reference.

The following examples are offered to further illustrate, but not limit, the compositions and methods of the invention.

EXAMPLE 1

Preparation of Neospora Vaccine

Maintenance of Neospora Cultures

Tachyzoites of the NC-1 strain of *N. caninum* were maintained in MARC-145 monkey kidney cell monolayers (USDA, ARS, Clay Center, Nebr.) in tissue culture flasks at 37° C. and 5% $CO_2$ in Opti-MEM™ medium (Gibco BRL) containing 1% (v/v) FBS, 100 U/ml penicillin, 100 $\mu$g/ml streptomycin, and 2 mM glutamine. Tachyzoites were harvested from infected cell cultures when about 60–90% of the MARC-145 host cells had lysed, as determined by microscopic examination of monolayers for cytopathic effects. Remaining infected cells containing intracellular tachyzoites were scraped off using a cell scraper and pooled with the culture medium containing the free, extracellular tachyzoites. The preparation (infected cells plus free tachyzoites) was centrifuged (1,876×g, 10 min, 4° C.), and the pellet was resuspended in 5 ml Hank's balanced salt solution (HBSS) (Gibco BRL). The suspension was passed five times through a 22 gauge needle, centrifuged as before, resuspended in 5 ml HBSS, and passed five times through a 28 gauge needle. Material was centrifuged as before, and the pellet resuspended in 5 ml HBSS. followed by passage through a sterile 5 $\mu$M filter to remove host cell debris. Material was centrifuged as before, the parasite pellet containing free tachyzoites was resuspended in HBSS, and the total number of viable tachyzoites was determined using a hemacytometer and trypan blue.

Preparation of Homogenate (Neospora Antigen)

Viable tachyzoites prepared as described above were adjusted to a cell density of $2\times10^8$/ml in Dulbecco's phosphate buffered saline (DPBS). For each 1 ml of tachyzoite suspension, 5 $\mu$l each of protease inhibitor stocks A and B were added. Protease inhibitor stock A contains 1 ml EDTA solution (prepared by adding 1.46 gm EDTA to 5 ml $H_2O$) and 4 ml $H_2O$. Protease inhibitor stock B contains 1 ml NEM (N-ethyl maleimide) solution (prepared by adding 312 mg NEM (Sigma Chemical Co.) to 2.5 ml ethanol), 1 ml pepstatin solution (prepared by adding 3.43 mg pepstatin (Sigma) to 5 ml ethanol), 3 ml PMSF (phenylmethylsulfonyl fluoride) solution (prepared by adding 291 mg PMSF (Sigma) to 5 ml ethanol), and 1 ml TPCK (N-tosyl-L-phenylalanine chloromethyl ketone) solution (prepared by adding 176 mg TPCK (Sigma) to 5 ml ethanol).

The tachyzoite preparation was frozen (−20° C.) and thawed (room temperature) three times, and then sonicated (Branson Sonifer 250, Branson Inc.) at a constant output (4 minutes/cycle) for three cycles on ice. The resulting homogenate was designated as a Neospora antigen (NSA) preparation. The protein concentration of the NSA preparation was determined using a commercial assay (Pierce BCA). NSA preparation aliquots were prepared and stored at −20° C. or −70° C. until further use in a vaccine and for in vitro assays (e.g., Western blot, cell proliferation). The NSA preparation did not contain any viable tachyzoites, as determined by lack of in vitro growth in MARC-145 cells and the inability to kill immunodeficient, nude mice.

Vaccine Formulation

The vaccine tested herein comprises the NSA preparation prepared as above and a veterinarily acceptable adjuvant. One of two different adjuvants, either SEAM62 or SEAM½, was used as adjuvant. SEAM62 is an oil-in-water emulsion containing 5% (v/v) squalene (Sigma), 1% (v/v) SPAN® 85 detergent (ICI Surfactants), 0.7% (v/v) TWEEN® 80 detergent (ICI Surfactants), 2.5% (v/v) ethanol, 200 $\mu$g/ml Quil A, 100 $\mu$g/ml cholesterol, 0.5% (v/v) lecithin, and 0.01% Thimerosal (Sigma). SEAM ½ is an oil-in-water emulsion containing 5% (v/v) squalene, 1% (v/v) SPAN® 85 detergent, 0.7% (v/v) Tween 80 detergent, 2.5% (v/v) ethanol, 100 µg/ml Quil A, 50 µg/ml cholesterol, and 0.01% Thimerosal.

Vaccines were prepared by adding equal volumes of the NSA preparation and adjuvant (SEAM62 or SEAM½), followed by gentle mixing, and were stored at 4° C. for primary and boost immunizations. Final vaccine protein concentration in both experiments was 250 µg NSA protein/ml. Control vaccines contained adjuvant alone (SEAM62 in Example 2, below; SEAM½ in Example 3, below).

EXAMPLE 2

Immunization and Challenge of Immunocompetent Mice

The purpose of this two-part study was to demonstrate the ability of a homogenate of Neopora cells, in this case tachyzoites of N. caninum strain NC-1, to induce a protective immune response in immunocompetent mice.

Figure 3:
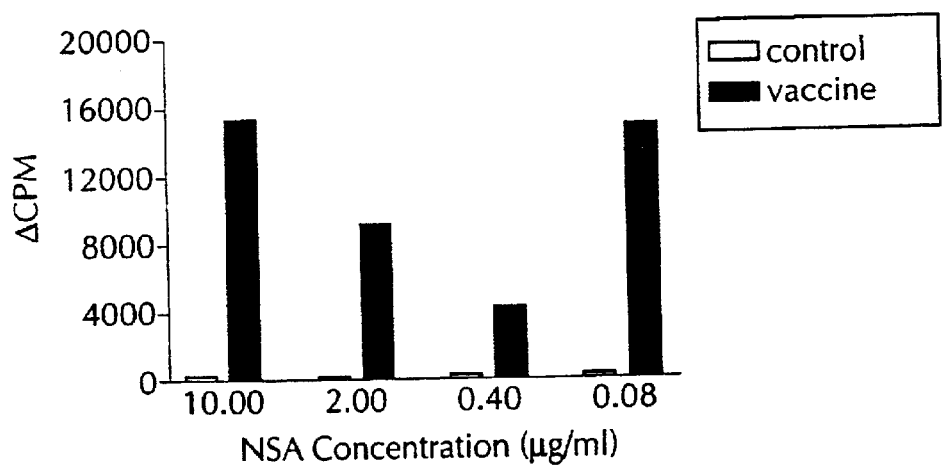
FIG. 3. Pre-challenge splenic antigen-specific proliferation assay. On day 21 post-immunization, splenocytes from mice administered adjuvant alone (control) or the NSA preparation plus adjuvant (vaccine) were prepared and T-cell proliferation assays conducted by incubating splenocytes in the presence of the NSA preparation and pulsing splenocyte cultures with [$^3$H]thymidine, as described below (Example 2). Results are expressed as $\Delta$ cpm (mean cpm with NSA minus mean cpm with medium alone), and demonstrate that a cell homogenate of Neospora can induce a T-cell population in vivo which is capable of proliferating in vitro following stimulation with the NSA preparation.

In the first part of the study, 8 week old female BALB/c mice (n=10/group) were immunized at day 0 and again at day 21 with either the SEAM62 adjuvant alone (control) or the NSA preparation plus the SEAM62 adjuvant (vaccine). Fifteen days after the last immunization, individual serum samples were randomly collected from 3 mice per group and stored at −20° C. for analysis of parasite-specific antibodies by Western blot (FIG. 1). The post-immunization Western blot analysis was conducted as follows. The NSA preparation was fractionated alongside molecular weight markers (Novex, San Diego, Calif.) under standard, nonreducing conditions by preparative gel electrophoresis (SDS-PAGE) using 12% sodium dodecyl sulfate-polyacrylamide precast gels (Novex). Following electrophoresis, separated proteins were transferred to PVDF membrane (Millipore, Bedford, Mass.), which was then rinsed in wash buffer (phosphate buffered saline (pH 7.5)/0.5% Tween 20 detergent), air-dried, and individual membrane strips cut (approx. 8 μg NSA protein/strip). Strips were incubated overnight at room temp. in blocking buffer (wash buffer containing 5% skim milk). Following two brief washes, strips were incubated for 1 hr at room temp. with primary antiserum samples (1:200 dilution in wash buffer) obtained at 15 days after the last immunization from either 3 individual adjuvant control mice (FIG. 1, lanes 1–3) or 3 vaccinated mice (FIG. 1, lanes 4–6). Following two rinses in wash buffer. strips were incubated with alkaline-phosphatase conjugated goat anti-mouse IgG (Kirkegaard & Perry) (1:10,000 dilution in wash buffer) for 1 hr at room temp, rinsed twice in wash buffer, and immunoreactive proteins detected using the chromogenic substrate BCIP/NBT (5-bromo-4-chloro-3-indolyl-phosphate/nitroblue tetrazolium) (Kirkegaard & Perry).

As shown in the Western blot in FIG. 1, serum antibodies collected from the three mice immunized with the NSA preparation plus adjuvant (lanes 4–6) were reactive with NSA preparation proteins having molecular weights of about 17–19, 28–30, 33, 37, 46, 48 and 56 kD. The immunoreactivity profiles of the serum samples from the three mice immunized with the NSA preparation plus adjuvant were essentially identical to each other and due to administration of the NSA preparation since no NSA-specific antibodies were detected in control mice administered adjuvant alone (lanes 1–3).

In the second part of the study, 4 week old female BALB/c mice (n=16/group) were immunized on days 0 and 14 with either the NSA preparation plus the SEAM½ adjuvant (vaccine), or with the SEAM½ adjuvant alone (control). Seven days after the last immunization, 4 donor mice were randomly selected from each group. Serum was collected from each mouse, pooled, and stored at −20° C. until testing by immunofluorescence. Splenocytes from donor groups were then prepared using standard procedures. Briefly, pooled spleens from each group were disrupted using tissue mesh sieves to obtain a single-cell suspension, and erythrocytes were lysed in Tris-buffered 0.83% $NH_4CI$. Following viable cell counts, aliquots from each of the two pooled splenocyte preparations (vaccine, control) were used for pre-challenge antigen-specific lymphocyte proliferation and cytokine assays as described below. Remaining pooled splenocytes were used for adoptive transfer into T-cell deficient. athymic mice (see Example 3, below). Remaining mice were subdivided into 4 groups (n=6/group) for subsequent challenge .

On day 22 post-immunization, groups (n=6/group) of BALB/c mice administered the NSA preparation plus SEAM½ adjuvant. or the SEAM½ adjuvant alone were challenged subcutaneously with either $1\times10^6$ or $1\times10^7$ NC-1 tachyzoites. Three weeks post-challenge, individual serum samples from all mice were collected, mice were euthanized, and tissues (spleen, lung and brain) individually collected for subsequent processing and assays as described below.

Pre- and post-challenge immunofluorescence antibody (IFA) titer assays were conducted as follows. Viable NC-1 tachyzoites ($5\times10^4$) were added to each well of a 96-well flat bottom plate. Wells were air-dried, and plates were stored at −20° C. until used. Serum test samples collected on day 21 post-immunization (day 0 challenge) and day 21 post-challenge were tested for IFA titers. Starting at an initial 1:50 serum dilution, serial twofold dilutions were added to wells and incubated for 30 min at room temperature. Following two washes in carbonate rinse buffer, wells were incubated with $(Fab)_2$ fluorescein isothiocyanate-conjugated anti-mouse IgG+IgM (Southern Biotechnology, Birmingham., Ala.). The plates were washed and 50 μl of 50% glycerol diluted in rinse buffer was added to each well. Plates were stored at 4° C. until viewed under a fluorescence microscope equipped with a filter for emission at 510 nm. Antibody titers are based on the highest dilution of immune serum producing detectable fluorescence.

Based on the results of the IFA titer assays, the vaccine of the invention is capable of inducing a humoral immune response resulting in the production of antibodies reactive against whole tachyzoites (FIG. 2). The mean IFA titer from 4 randomly pooled serum samples from mice immunized with vaccine was >25,000 compared to a mean titer of <50 using pooled sera from control mice. Post-challenge geometric mean titers were significantly higher in vaccinated animals than in controls (P<0.001) and higher than pre-challenge titers, indicating that the vaccine induced a memory immune response in vaccinated animals that was boosted upon subsequent parasite challenge.

The ability of the NSA preparation to induce cellular (T-cell) immune responses was determined as follows. Seven days after the last immunization, mice injected only with adjuvant (control) and mice injected with the NSA preparation plus adjuvant (vaccine) were euthanized and their spleens removed. Pooled spleens (4 per group) were disrupted using tissue mesh sieves to obtain a single-cell suspension, followed by lysis of erythrocytes in Tris-buffered 0.83% $NH_4CI$. Following viable cell counts, cells were suspended in complete RPMI 1640 medium containing 10% heat-inactivated FBS, penicillin (100 U/ml), streptomycin (100 μg/ml), $5\times10^{-5}$ M β-mercaptoethanol, 2 mM L-glutamine, 5 µg/ml insulin, 10 µg/ml transferrin, and 10 µg/ml selenium. For proliferation assays, cells were plated in 96-well flat-bottomed plates at $5 \times 10^5$ cells per well. Cells were incubated with complete medium with or without 5-fold serial dilutions of the NSA preparation starting at 10 µg NSA protein/ml in quadruplicate wells in a final volume of 200 µl. Plates were incubated at 37° C. in 7% $CO_2$ for 72 hr. Proliferation of T lymphocytes was assessed by pulsing splenocyte cultures with 0.33 µCi of [$^3$H]thymidine for an additional 18 to 24 hr. Cells were harvested onto filters using a MACHIII cell harvester (TomTech, Orange, Conn.), and incorporation of radioactivity was determined with a scintillation counter (Wallac, Turku, Finland). Results are expressed in FIG. 3 as Δ cpm (mean cpm with NSA minus mean cpm with medium alone).

Splenocytes from vaccinated mice. but not from control mice, proliferated in vitro following stimulation with the NSA preparation. These in vitro cell proliferation assay results demonstrate that the vaccine of the present invention can induce cellular (T-cell) immune responses.

For cytokine assays, cells were plated in 96-well flat-bottomed plates at $5 \times 10^5$ cells per well. Cells were incubated with complete medium with or without the NSA preparation (10 µg NSA protein/ml final concentration) in quadruplicate wells in a final volume of 200 µl. Plates were incubated at 37° C. in 7% $CO_2$, and cell-free supernatants collected at 24 hr intervals for 4 days and stored at −20° C. until testing. The presence of specific cytokines in collected samples was determined by two-site immunosorbent assay (ELISA) using a panel of commercial cytokine-specific unconjugated and conjugated antibodies, recombinant cytokine standards and protocols suggested by the manufacturer (PharMingen, San Diego, Calif.). Results are expressed as pg/ml in which the background cytokine activity in wells of cells incubated without NSA was subtracted.

Figure 4:
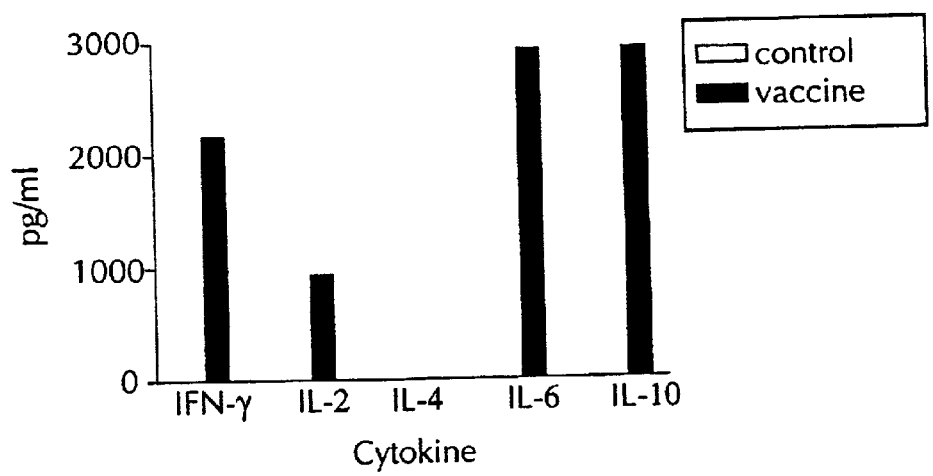
FIG. 4. Donor pre-challenge splenic antigen-specific cytokine production. On day 21 post-immunization, splenocytes from mice administered adjuvant alone (control) or the NSA preparation plus adjuvant (vaccine) were prepared and levels of cytokine production determined by incubating splenocytes in the presence of the NSA preparation, collecting cell-free supernatants and assaying for specific cytokines using commercial cytokine-specific antibodies following manufacturer's instructions (PharMingen, San Diego, Calif.). Results demonstrate that a cell homogenate of Neospora can induce a T-cell population in vivo which is capable of producing both type-1 (IFN-$\gamma$, IL-2) and type-2 (IL-6, IL-10) cytokines in vitro following stimulation with the NSA preparation.

Donor pre-challenge splenic antigen-specific cytokine production is shown in FIG. 4, demonstrating that the vaccine of the present invention can induce both type 1 (IFN-γ, IL-2) and type 2 (IL-6, IL-10) cellular immune responses following immunization. The induction of IFN-γ is especially noteworthy, as this cytokine has recently been demonstrated to play a protective role against murine neosporosis, (Khan et al., 1997, Experimental Parasitology, 85:24–34). Moreover, IFN-γ appears to be required for host protection against the related Apicomplexa parasite, *T. gondii* (Suzuki et al., 1988, Science 240:516–518). The induction of IFN-γ by the vaccine of the present invention may also be involved in the vaccine's ability to protect immunocompetent mice, as well as in it's ability to induce memory T cells capable of secreting IFN-γ following adoptive transfer of such cells into immunodeficient athymic mice, as described below in Example 3. The ability of the killed vaccine to induce IL-6 and IL-10 may also be important in the vaccine's ability to protect against neosporosis since both cytokines have been shown to play an important role in host protection against *T. gondii* (Suzuki et al., 1997, Infect. Immun. 65: 2339–2345.; Neyer et al. 1997. Infect. Immun., 65:1675–1682).

Figure 5A:
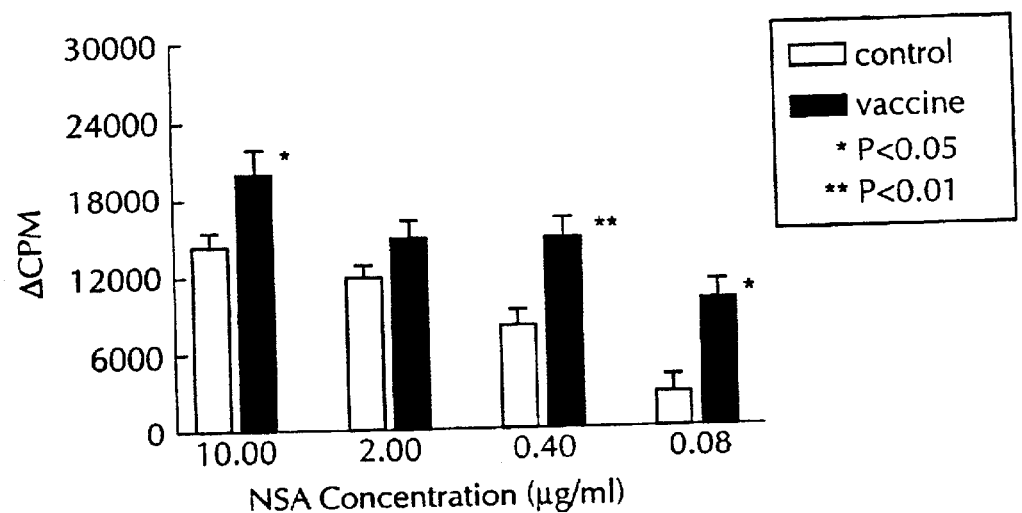
FIGS. 5A–5B Post-challenge splenic antigen-specific proliferation assay. At day 21 post-challenge, splenocytes from BALB/c mice administered adjuvant alone (control) or the NSA preparation plus adjuvant (vaccine) were prepared and T-cell proliferation assays conducted by pulsing splenocyte cultures with [3H]thymidine as described below. Following challenge with $1\times10^6$ (A) or $1\times10^7$ (B) NC-1 tachyzoites, significantly higher antigen-specific responses (*=$P<0.05$; **=$P<0.01$) were detected using splenocytes from vaccinated mice compared to control mice (n=4/group).
Figure 5B:
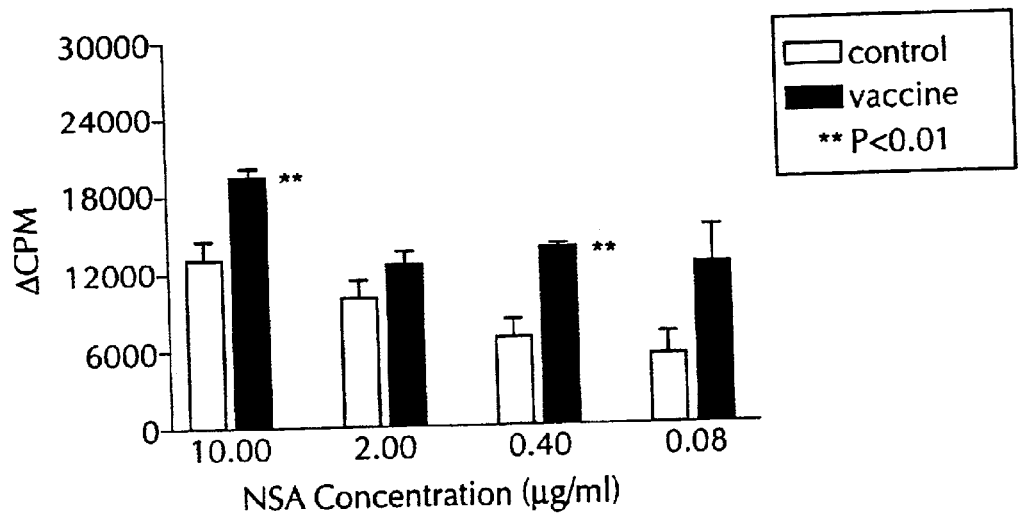
Figure 6A:
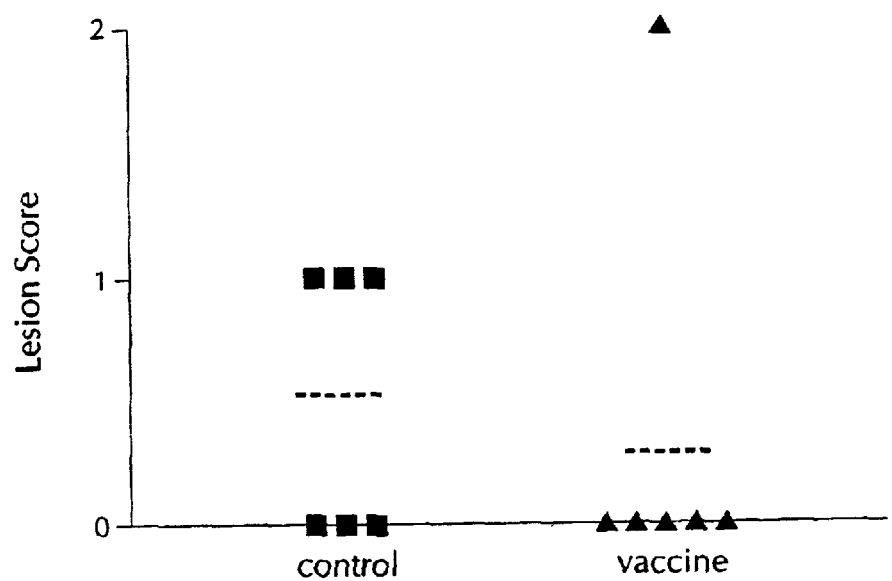
FIGS. 6A–6D Post-challenge lung (A, C) and brain (B, D) lesion scores. Sections of lung and brain tissue from day 21 post-challenge control (n=6) and vaccine (n=6) BALB/c mice challenged with either $1\times10^6$ (A, B) or $1\times10^7$ (C, D) NC-1 tachyzoites were prepared and scored as described below. Lesion scores for individual animals are presented. Dotted line represents mean lesion score for each group. Results demonstrate that animals immunized with a cell homogenate of Neospora and challenged with $1\times10^7$ NC-1 tachyzoites have significantly lower mean lung ($p<0.01$) and brain ($P<0.05$) lesions scores compared to challenge controls. A. control mean=0.5, vaccine mean=0.33. B. control mean=1.0, vaccine mean=0.33. C. control mean=1.83, vaccine mean=0.67 ($P<0.01$). D. control mean=1.83, vaccine mean=1.0 ($P<0.05$).
Figure 6B:
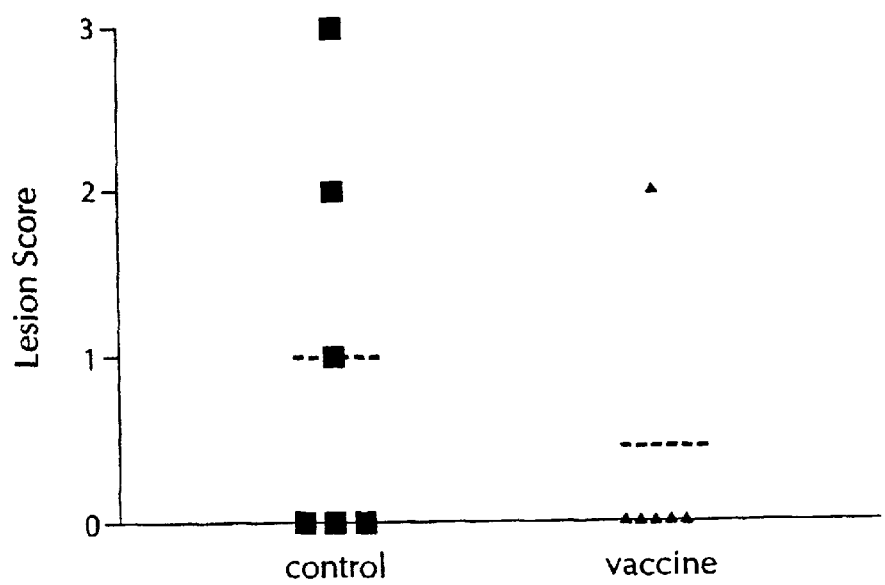
Figure 6C:
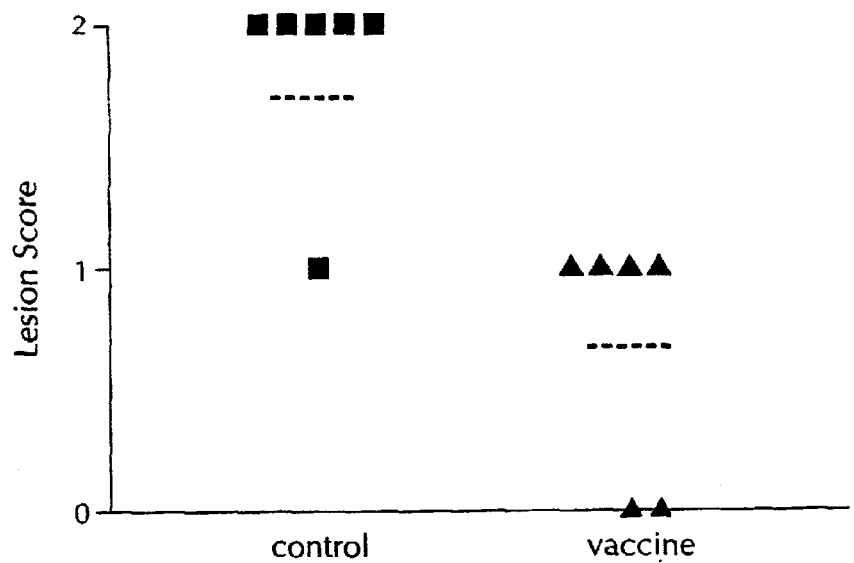
Figure 6D:
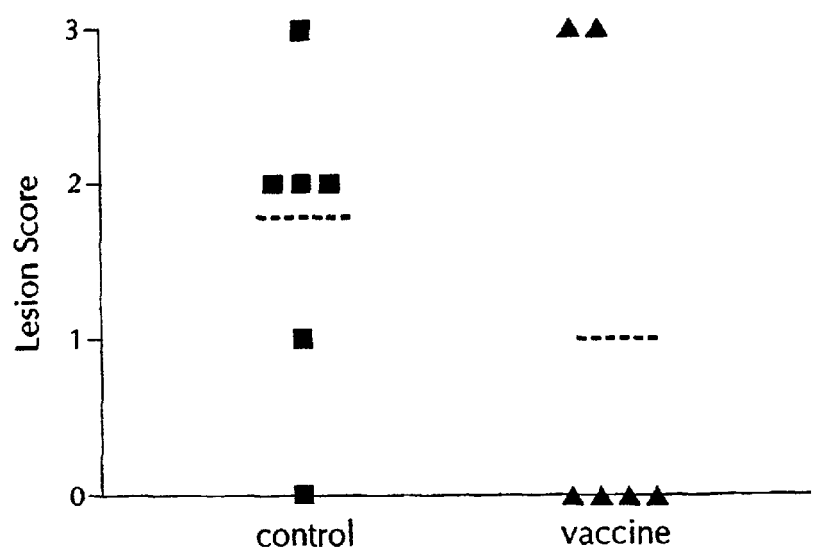

The ability of the vaccine of the present invention to induce cellular (T-cell) immune responses was further established by examining day 21 post-challenge splenic antigen-specific proliferation, as described above for day 21 post-immunization mice. As shown in FIG. 5, T-lymphocyte responses to the NSA preparation following challenge with either $1 \times 10^6$ or $1 \times 10^7$ NC-1 tachyzoites were significantly higher (P<0.01, P<0.05) in vaccinated animals than in controls.

The ability of the vaccine of the invention to protect animals against Neospora-induced encephalitis was determined by measuring the number of lesions in lung and brain tissue sections following infection of vaccinated and control mice at 2 different challenge doses. On day 21 post-challenge, lung and brain tissues were individually collected (6/group) and fixed in 10% neutral buffered formalin, sectioned, and stained with hematoxylin and eosin using routine histological techniques. Stained lung and brain sections were coded and scored in a blinded fashion without prior knowledge of treatment. Lung and brain lesions were scored using the following system: (0) within normal limits, (1) slight, (2) mild, (3) moderate, (4) severe and (5) marked.

Post-challenge brain and lung lesion scores from BALB/c mice are presented in FIGS. 6(*a–d*), demonstrating that animals immunized with the vaccine of the present invention have significantly lower mean lung (p<0.01) and brain (P<0.05) lesions compared to controls following a parasite challenge of $1 \times 10^7$ NC-1 tachyzoites. In addition, mean brain and lung lesion scores are numerically higher in control mice compared to vaccinated mice following a parasite challenge of $1 \times 10^6$ NC-1 tachyzoites. The lack of statistically significant difference in lesion scores between vaccinated and control mice at the $1 \times 10^6$ challenge dose can be attributed to one outlier mouse in the vaccine group, which had both a lung and brain score of 2.

EXAMPLE 3

Challenge of Immunodeficient Mice Following Adoptive Transfer of Splenocytes

The purpose of this study was to determine if splenic lymphocytes from vaccinated, immunocompetent mice could be used to adoptively transfer protection to T-cell immunodeficient athymic mice (nu/nu or 'nude' mice, Charles River Labs), as demonstrated by a prolongation of survival following a virulent, NC-1 challenge.

Each nude mouse (n=7/group) received an intravenous injection of $1 \times 10^7$ splenocytes (in 0.1 ml DPBS) obtained from either vaccinated or adjuvant control BALB/c mice seven days after the last immunization. Control nu/nu mice received only DPBS (0.1 ml). On day 22 (24 hr post-transfer), all nude mice were challenged subcutaneously with $5 \times 10^6$ NC-1 tachyzoites. Challenged nude mice were monitored for clinical signs of neosporosis and death beginning on day 14 post-challenge.

Post-challenge survival curves of athymic nude mice are presented in FIG. 7. Nude mice which received DPBS alone (no splenocytes="no cells") were highly susceptible to challenge with NC-1 tachyzoites. By day 21 post-challenge, none of the mice in this group survived. Nude mice receiving splenocytes from BALB/c mice that were injected either with the NSA preparation plus adjuvant or adjuvant alone lived longer. Eighty percent of nude mice receiving splenocytes from BALB/c mice that were injected with adjuvant alone eventually succumbed to their infection, and only 1 mouse in this group was alive at the termination of the experiment (day 48 post-challenge). By contrast, 100% of nude mice receiving splenocytes from BALB/c mice that were injected with the NSA preparation plus adjuvant survived parasite challenge through the entire experimental period. These results demonstrate that splenocytes from vaccinated donors are capable of conferring adoptive protective immunity against neosporosis, and provide further evidence for the efficacy of the vaccine of the present invention.

All patents, patent applications, and publications cited above are incorporated herein by reference in their entirety.

The present invention is not limited in scope by the specific embodiments described, which are intended as single illustrations of individual aspects of the invention. Functionally equivalent compositions and methods are within the scope of the invention. Indeed, various modifications of the invention, in addition to those shown and described herein, will become apparent to those skilled in the art from the foregoing description. Such modifications are intended to fall within the scope of the appended claims.

We claim:

1. A method for protecting a mammal against neosporosis comprising administering to the mammal a vaccine comprising an immunologically effective amount of a homogenate and a veterinarily acceptable carrier, wherein said homogenate is prepared by homogenizing or disrupting a whole cell preparation of Neospora tachyzoites and said homogenate is free of viable tachyzoites, and wherein said homogenate is capable of inducing a protective response against neosporosis in a mammal.

2. The method of claim 1, wherein the species of Neospora from which the homogenate is prepared is *N. caninum*.

3. The method of claim 1, wherein the vaccine is capable of inducing the production of antibodies that recognize one or more antigenic components present in an homogenate of cells *N. caninum* strain NC-1.

4. The method of claim 2, wherein the strain of *N. caninum* from which the homogenate of the vaccine is prepared is NC-1.

5. The method of claim 1, wherein the vaccine further comprises one or more additional immunomodulatory components.

6. The method of claim 5, wherein the additional immunomodulatory component is an adjuvant.

7. The method of claim 5, wherein the additional immunomodulatory component is a cytokine.

8. The method of claim 1, wherein the vaccine is administered to a mammal of a species selected from the group consisting of dogs, cows, goats, sheep and horses.

9. The method of claim 1, wherein said homogenate is made by homogenizing or disrupting a whole cell preparation of Neospora tachyzoites by freeze-thawing, osmotic bursting, grinding, sonication, use of a polytron, blender, tissue homogenizer, or a combination thereof.

* * * * *